US010464051B2

(12) United States Patent
Partington

(10) Patent No.: US 10,464,051 B2
(45) Date of Patent: Nov. 5, 2019

(54) PROCESS FOR PRODUCING ALKENES FROM OXYGENATES BY USING SUPPORTED PARTIALLY NEUTRALISED HETEROPOLYACID CATALYSTS

(71) Applicant: TECHNIP E&C LIMITED, Milton Keynes, Buckinghamshire (GB)

(72) Inventor: Stephen Roy Partington, Hull (GB)

(73) Assignee: TECHNIP E&C LIMITED, Milton Keynes, Buckinghamshire (GB)

(*) Notice: Subject to any disclaimer, the term of this patent is extended or adjusted under 35 U.S.C. 154(b) by 32 days.

(21) Appl. No.: 15/537,823

(22) PCT Filed: Dec. 18, 2015

(86) PCT No.: PCT/EP2015/080477
§ 371 (c)(1),
(2) Date: Jun. 19, 2017

(87) PCT Pub. No.: WO2016/097287
PCT Pub. Date: Jun. 23, 2016

(65) Prior Publication Data
US 2017/0354959 A1    Dec. 14, 2017

(30) Foreign Application Priority Data
Dec. 19, 2014  (EP) ................................... 14199352

(51) Int. Cl.
*B01J 27/188* (2006.01)
*B01J 37/02* (2006.01)
(Continued)

(52) U.S. Cl.
CPC .............. *B01J 27/188* (2013.01); *B01J 23/30* (2013.01); *B01J 37/0205* (2013.01); *C07C 1/24* (2013.01);
(Continued)

(58) Field of Classification Search
CPC ...... B01J 27/188; B01J 23/30; B01J 37/0205; C07C 1/24
See application file for complete search history.

(56) References Cited

U.S. PATENT DOCUMENTS

2012/0165589 A1* 6/2012 Partington ................ C07C 1/24
585/639

FOREIGN PATENT DOCUMENTS

WO    WO 2008/062157 A1    5/2008
WO    WO 2008/138775 A1    11/2008

OTHER PUBLICATIONS

International Search Report for International Application No. PCT/EP2015/080477 dated Mar. 4, 2016.

* cited by examiner

*Primary Examiner* — Melvin C. Mayes
*Assistant Examiner* — Michael Forrest
(74) *Attorney, Agent, or Firm* — David W. Carstens; J. Andrew Reed; Carstens & Cahoon, LLP

(57) ABSTRACT

A process for the vapour phase chemical dehydration of ethanol in a reactor in the presence of a supported heteropolyacid catalyst, said process comprising a step of contacting the ethanol with the heteropolyacid catalyst, wherein the heteropolyacid catalyst comprises a partially neutralised silicotungstic acid salt, wherein the partially neutralised silicotungstic acid salt has from 30% to 70% of the hydrogen atoms replaced with cations selected from the group consisting of alkali metal cations, alkaline earth metal cations, transition metal cations, ammonium cations, and mixtures thereof; but with the proviso that the alkali metal cation is not lithium; and wherein, after attaining steady-state performance of the catalyst, said process is operated continuously (Continued)

Figure 1:
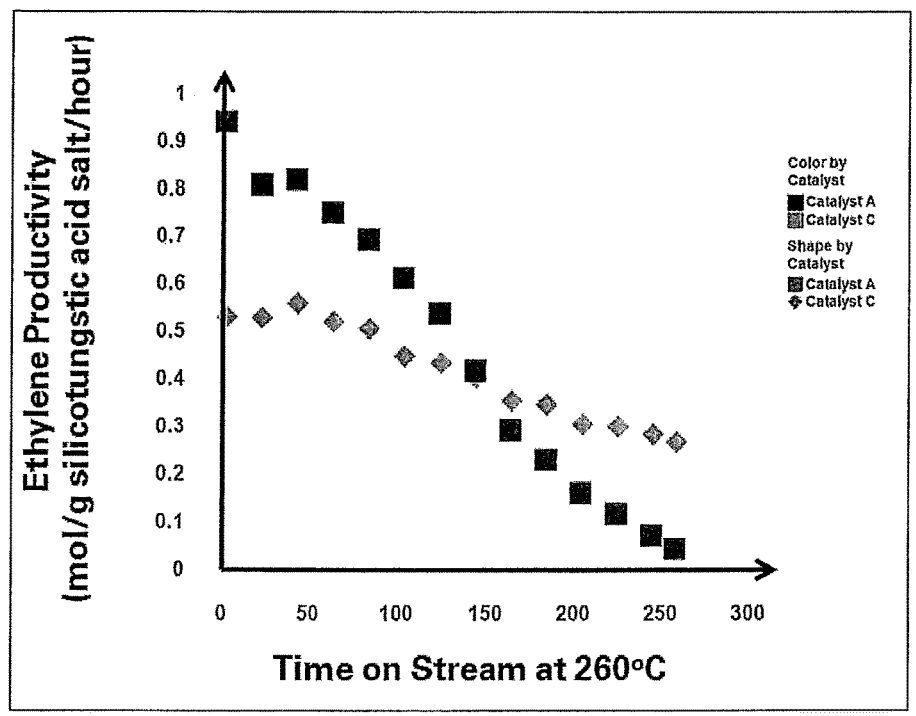

with the same supported heteropolyacid catalyst for at least 150 hours, without any regeneration of the catalyst.

16 Claims, 3 Drawing Sheets

(51) Int. Cl.
    *B01J 23/30*     (2006.01)
    *C07C 1/24*     (2006.01)
(52) U.S. Cl.
    CPC ...... *C07C 2521/08* (2013.01); *C07C 2523/04* (2013.01); *C07C 2523/30* (2013.01); *C07C 2527/188* (2013.01)

PROCESS FOR PRODUCING ALKENES FROM OXYGENATES BY USING SUPPORTED PARTIALLY NEUTRALISED HETEROPOLYACID CATALYSTS

The field of the invention is the dehydration of oxygenates to alkenes. The present invention relates to a process for producing ethene by the vapour phase dehydration of ethanol using a heteropolyacid catalyst. In particular, the present invention involves the use of a partially neutralised heteropolyacid catalyst, which has been found to exhibit extended catalyst lifetime in an alcohol dehydration process, in particularly in an ethanol dehydration reaction, compared with conventional heteropolyacid catalysts.

Ethene is an important commodity chemical and monomer which has traditionally been produced industrially by the steam or catalytic cracking of hydrocarbons derived from crude oil. However there remains an increasing need to find alternative economically viable methods of making this product. By virtue of its ready availability from the fermentation of biomass and synthesis gas based technologies, ethanol is emerging as an important potential feedstock from which ethene can be made in the future.

The production of ethene by the vapour phase chemical dehydration of ethanol is a well-known chemical reaction which has been operated industrially for many years (see for example Kirk Othmer Encyclopaedia of Chemical Technology (third edition), Volume 9, pages 411 to 413). Traditionally this reaction has been carried out in the presence of an acid catalyst such as activated alumina or supported phosphoric acid.

In recent years attention has turned to finding alternative catalysts having improved performance. This has led to the use of supported heteropolyacid catalysts, such as those disclosed in EP1925363, in the vapour phase chemical dehydration of a feedstock comprising ethanol and ethoxyethane for the production of ethene. Use of such catalysts provides improved selectivity, improved productivity and reduced ethane formation. The latter is particularly desirable because firstly ethane is an undesirable by-product and secondly its separation from ethene on a large scale is both difficult and energy intensive. Related documents WO 2007/063281 and WO 2008/062157 also disclose methods of carrying out dehydration of oxygenate feedstocks with supported heteropolyacid catalysts.

In the ethanol dehydration process, a feed typically comprising ethanol, optionally water and other components (e.g. ethoxyethane) is continuously fed to a reactor containing a bed of heteropolyacid catalyst and the products continuously removed. Under steady state conditions, the feed entering the reactor is rapidly converted near the inlet into an equilibrium mixture of water, ethanol and ethoxyethane (the product of a rapid first stage dehydration of the ethanol). Such processes are typically conducted at elevated temperature and pressure.

It is known that oxygenate dehydration can lead to carbon build-up on acidic catalysts, such as silicotungstic-$SiO_2$, which leads to catalyst deactivation. Carbon lay-down leading to heteropolyacid catalyst deactivation is, for instance, mentioned in WO 2008/138775. That document also indicates that the partial replacement of hydrogen atoms of the heteropolyacid catalyst with potassium cations was found to reduce the stability of the catalyst still further.

It has now surprisingly been found that heteropolyacid catalyst lifetime can be advantageously extended by the partial replacement of hydrogen atoms of the heteropolyacid catalyst with other cations by partial neutralisation. Contrary to what is suggested in the prior art, a specific degree of partial replacement of the hydrogen atoms of a heteropolyacid catalyst with other cations has been found to result in increased catalyst lifetimes for an ethanol dehydration process. Partially neutralised heteropolyacid salts are known to be of use as catalysts, but their extended lifetime in an ethanol dehydration reaction has hitherto not been appreciated.

Thus, according to a first aspect, the present invention provides a process for the preparation of ethene by vapour phase chemical dehydration of ethanol in a reactor, said process comprising a step of contacting the ethanol with the heteropolyacid catalyst, wherein the partially neutralised heteropolyacid catalyst is a silicotungstic acid with from 30% to 70% of the hydrogen atoms replaced by cations selected from the group consisting of alkali metal cations, alkaline earth metal cations, transition metal cations, ammonium cations, and mixtures thereof, but with the proviso that the alkali metal cation is not lithium. After attaining steady-state performance of the catalyst, the process of the present invention is operated continuously with the same supported heteropolyacid catalyst for at least 150 hours, without any regeneration of the catalyst.

In a preferred embodiment of the first aspect of the present invention, the process is operated continuously with the same supported heteropolyacid catalyst for at least 200 hours, more preferably for at least 250 hours, even more preferably for at least 300 hours, or even longer, such as at least 500, at least 1000, at least 2000 or at least 5000 hours, without any regeneration of the catalyst.

In some embodiments of the present invention, the silicotungstic acid catalyst retains at least 25% of its maximum activity, preferably at least 50% of its maximum activity, more preferably at least 75% of its maximum activity and even more preferably at least 85% of its maximum activity observed for the operating temperature under steady-state conditions (i.e. under constant reaction conditions), after at least 200 hours of operation of the process, preferably after at least 250 hours of operation of the process, more preferably at least 300 hours, or any other of the operating times in the paragraph above. Any combination of the operating times and activity percentages herein may be made. The catalyst activity is determined as an average across the catalyst bed based on the overall productivity of the bed.

According to a second aspect, the present invention provides a process for the preparation of ethene by vapour phase chemical dehydration of ethanol in a reactor, wherein the partially neutralised heteropolyacid catalyst is a phosphotungstic acid with from 10% to 40% of the hydrogen atoms replaced by cations selected from the group consisting of alkali metal cations, alkaline earth metal cations, transition metal cations, ammonium cations, and mixtures thereof, but with the proviso that the alkali metal cation is not lithium. After attaining steady-state performance of the catalyst, the process of the present invention is operated continuously with the same supported heteropolyacid catalyst for at least 150 hours, without any regeneration of the catalyst.

In a preferred embodiment of the second aspect of the present invention, the process is operated continuously with the same supported heteropolyacid catalyst for at least 200 hours, more preferably for at least 250 hours, and even more preferably for at least 300 hours, or even longer, such as at least 500, at least 1000, at least 2000 or at least 5000 hours, without any regeneration of the catalyst.

In some embodiments of the present invention, the phosphotungstic acid catalyst retains at least 25% of its maximum activity %, preferably at least 50%, more preferably at least 75% and even more preferably at least 85% of its maximum activity, observed for the operating temperature under steady-state conditions (i.e. under constant reaction conditions), after at least 100 hours of operation of the process, preferably at least 150 hours of operation of the process, more preferably at least 200 hours of operation of the process, even more preferably at least 250 hours of operation of the process, even more preferably still at least 300 hours or any other of the operating times in the paragraph above. Any combination of the operating times and activity percentages herein may be made. The catalyst activity is determined as an average across the catalyst bed based on the overall productivity of the bed.

Reference herein to the "steady-state performance" of the heteropolyacid catalyst is intended to mean the point at which a constant level of activity and selectivity of the catalyst is achieved under the operating conditions of the process, where "constant level" means that there is 5% or less change in activity and selectivity over a period of at least 5 hours of operation. Preferably, there is 2% or less change in activity and selectivity, more preferably 1% or less, even more preferably 0.5% or less, most preferably 0.1% or less, for example 0%, over a period of at least 5 hours of operation. Once steady-state performance of the heteropolyacid catalyst has been attained, it may be desirable to subsequently change operating conditions during a run (for example, pressure and/or temperature) and thereby modify the selectivity and/or activity of the catalyst. However, changes in operating conditions following attainment of steady-state performance do not affect the calculation of the time period for operation with the same catalyst in accordance with the present disclosure. For the avoidance of doubt, the time period referred to herein for operation with the same catalyst without regeneration thereof begins upon the attainment of initial steady-state performance of the catalyst and ends once operation of the dehydration process with the catalyst substantially ceases, for instance in order to conduct catalyst regeneration or shut down the reactor such as for catalyst replacement.

The term "regeneration" used herein refers to the process of re-activating a heteropolyacid catalyst material that has become deactivated (e.g. by coke deposition thereon) by, for instance, coke combustion procedures or the like, or extracting heteropolyacid from a used catalyst for preparing a fresh catalyst.

Heteropolyacids having the degree of partial neutralisation according to the above described aspects of the present invention exhibit significantly extended catalyst lifetime in comparison to alternative or otherwise conventional heteropolyacid catalysts. This has clear economic benefits relating to re-use and replacement of the catalyst, as well as the reduction of waste.

Without being bound by any particular theory, neutralisation of the supported heteropolyacid catalysts discussed hereinbefore is believed to modify the dominant surface chemistry of the supported catalyst such that its propensity for deactivation, for instance by carbon lay-down and other deactivation mechanisms, is reduced.

Thus, in another aspect, the present invention also provides a use of a supported partially neutralised heteropolyacid salt catalyst for increasing catalyst lifetime in an alcohol dehydration process, preferably an ethanol dehydration process, with the proviso that partially neutralised heteropolyacid catalyst is not partially neutralised with lithium cations.

The dehydration of the feedstock according to the present invention is believed (Chem. Eng Comm. 1990, 95, 27 to 39) to proceed by either the direct dehydration to olefin(s) and water (such as illustrated in relation to the dehydration of ethanol in Equation 1); or via an ether intermediate (such as illustrated in relation to the etherification of ethanol and dehydration of ethoxyethane in Equations 2 and 3).

(1)

(2)

(3)

The direct conversion of the ether to two moles of olefin and water has also been reported (Chem. Eng. Res. and Design 1984, 62, 81 to 91). All of the reactions shown above are typically catalysed by Lewis and/or Bronsted acids. Equation 1 shows the endothermic direct elimination of ethanol to ethene and water; competing with Equation 1 are Equations 2 and 3 i.e. the exothermic etherification reaction (Equation 2), and the endothermic elimination of ethoxyethane to produce ethene and ethanol (Equation 3). However, the dehydration reaction of ethanol to ethene is overall said to be endothermic.

The present invention provides a process for the preparation of ethene by vapour phase chemical dehydration of ethanol, said process comprising contacting the feed-stream comprising ethanol with a supported partially neutralised heteropolyacid catalyst in a reactor. Preferably, the feed-stream comprising ethanol further comprises water and/or ethoxyethane, more preferably water and ethoxyethane.

Suitably, in the aspects and embodiments of the present invention which relate to the vapour phase dehydration of ethanol, the amount of water in the feed-stream is at most 50 wt %, more preferably at most 20 wt %, most preferably at most 10 wt %, or even at most 7 wt %, based on the total weight of water, ethanol and ethoxyethane in the reactant feed-stream. Preferably, the amount of water in the feed-stream is at least 0.1 wt %, more preferably at least 0.5 wt % and most preferably at least 1 wt %, based on the total weight of water, ethanol and ethoxyethane in the feed-stream.

Suitably, in the aspects and embodiments of the present invention which relate to the vapour phase dehydration of ethanol, the amount of ethoxyethane in the feed-stream is at most 50 wt. %, more preferably at most 40 wt. %, most preferably at most 35 wt. %, based on the total weight of water, ethanol and ethoxyethane in the feed-stream. Preferably, the amount of ethoxyethane in the feed-stream is at least 0.1 wt. %, more preferably at least 0.5 wt. % and most preferably at least 1 wt. %, based on the total weight of water, ethanol and ethoxyethane in the feed-stream.

The liquid product stream following olefin removal comprises mostly unreacted alcohols, ethers and water. In the aspects and embodiments of the present invention which relate to the vapour phase dehydration of ethanol, the liquid product stream following ethene removal comprises mostly unreacted ethanol, ethoxyethane and water. The applicants have found that it is particularly preferable to recycle the major portion of the alcohols and ethers back to the vapour phase dehydration reactor after water removal.

In some embodiments of the invention, the feed-stream comprises an inert diluent. In other embodiments, an inert diluent is added down the catalyst bed, or between multiple catalyst beds arranged in series or in parallel, if used. Preferred diluents comprise nitrogen, helium, ethene and/or saturated hydrocarbons, for example hexanes, 2-methylpropane or n-butane. More preferably, the feed-stream diluent is selected from nitrogen and/or helium.

The operating conditions under which the dehydration process is conducted are typically such that the dehydration process is always operated in a vapour phase state. In a preferred embodiment, therefore, the operating pressure of the dehydration process is suitably always at least 0.1 MPa, preferably 0.2 MPa, below the dew point pressure and/or the dehydration process operating temperature is at least 10° C. above the dew point temperature of the feed-stream entering the vapour phase dehydration reactor and the reaction mixture that is present inside the vapour phase dehydration reactor. The latter is dependent on factors such as the initial feed-stream composition and the degree of conversion within the reactor.

For the purposes of the present invention, the 'dew point temperature' is defined as being a threshold temperature. For example, for a given mixture, at a given pressure, if the system temperature is raised to above the dew point temperature, the mixture will exist as a dry gas. Likewise below the dew point temperature, the mixture will exist as a vapour containing some liquid. And similarly the 'dew point pressure', is defined as being a threshold pressure. For example, for a given mixture, at a given temperature, if the system pressure is below the dew point pressure, the mixture will exist as a dry gas; above the dew point pressure, the mixture will exist as a vapour containing some liquid.

Thus, in some embodiments of the present invention, the feed temperature of a feed-stream comprising ethanol is preferably from 180° C. to 270° C., more preferably from 190° C. to 260° C. and most preferably from 200° C. to 260° C. Reference to "feed temperature" herein is intended to refer to the temperature of a particular stream at the point at which it is fed to the reactor. The vapour phase reactor used for dehydrating the oxygenates is preferably operated at an internal pressure of from 0.1 MPa to 4.5 MPa, more preferably at a pressure of from 1.0 MPa to 3.5 MPa, still more preferably at a pressure of from 2.0 MPa to 3.5 MPa, and most preferably at a pressure of from 2.5 MPa to 3.3 MPa.

In other preferred embodiments of the present invention, the feed temperature of a feed-stream comprising ethanol is preferably at least 220° C., more preferably at least 240° C. In some particular preferred embodiments, the feed temperature is at least 252° C., at least 255° C., at least 260° C., at least 280° C. or even at least 300° C. In the aspects and embodiments of the present invention which relate to the vapour phase dehydration of ethanol, the upper limit of the feed temperature is below the temperature at which selectivity for ethene is negatively impacted and/or one which is overly energy intensive. Preferably, the upper limit of the feed temperature of the feed-stream is 350° C., more preferably 325° C. In these embodiments, the reactor preferably has an internal pressure of from 0.90 MPa to 1.60 MPa, more preferably from 0.95 MPa to 1.30 MPa, and most preferably from 1.00 MPa to 1.20 MPa.

A partially neutralised heteropolyacid salt according to the present invention is deemed to include heteropolyacid salts wherein the hydrogen atoms of a free heteropolyacid precursor are replaced with other suitable cations. Such partially neutralised heteropolyacid salts may be obtained by the reaction of a free heteropolyacid precursor with a base, wherein the base may comprise a salt including the cation with which it is desired to replace the hydrogen atoms of the free heteropolyacid precursor. The term "free heteropolyacid", as used herein and throughout the description of the present invention, is deemed to refer to a heteropolyacid wherein substantially none of the hydrogen atoms are replaced by other cations.

Suitable cations with which the hydrogen atoms of a free heteropolyacid precursor may be replaced include alkali metal, alkaline earth metal, ammonium, transition metal cations, or mixtures thereof. The term "ammonium" as used herein and throughout the description is intended to refer to $[NH_4]^+$ cations, as well as alkyl ammonium cations of general formula $[NH_xR_{4-x}]^+$, wherein x<4 and each of the groups R is independently selected from $C_1$ to $C_8$ alkyl groups.

In some aspects of the invention, the partially neutralised heteropolyacid salts may be any complex, high molecular weight anions comprising oxygen-linked polyvalent metal atoms. Typically, each anion comprises about 12 to about 18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable free heteropolyacid precursors include Keggin, Wells-Dawson and Anderson-Evans-Perloff heteropolyacids. Examples of suitable free heteropolyacid precursors that can be partially neutralised are as follows:

18-tungstophosphoric acid—$H_6[P_2W_{18}O_{62}].xH_2O$
12-tungstophosphoric acid—$H_3[PW_{12}O_{40}].xH_2O$
12-tungstosilicic acid—$H_4[SiW_{12}O_{40}].xH_2O$
Phosphomolybdic acid—$H_3[PMo_{12}O_{40}].xH_2O$
Silicomolybdic acid—$H_4[SiMo_{12}O_{40}].xH_2O$
Diphosphomolybdic acid—$H_6[P_2Mo_{18}O_{62}].xH_2O$ The preferred partially neutralised heteropolyacid salt for use in the process described by the present invention is any partially neutralised free heteropolyacid precursor that is based on the Keggin or Wells-Dawson structures; more preferably the chosen free heteropolyacid precursor for use in the process described by the present invention is any of the following: heteropolytungstic acid (such as silicotungstic acid (STA) and phosphotungstic acid (PTA)), silicomolybdic acid and phosphomolybdic acid. As discussed hereinbefore, the ethanol dehydration catalyst according to the first and second aspects of the present invention comprise a supported partially neutralised silicotungstic acid salt or a supported partially neutralised phosphotungstic acid salt, respectively. Thus, most preferably, the chosen free heteropolyacid precursor for use in the process described by the present invention is silicotungstic acid, for example 12-tungstosilicic acid ($H_4[SiW_{12}O_{40}].xH_2O$), or phosphotungstic acid, for example 12-tungstophosphoric acid ($H_3[PW_{12}O_{40}].xH_2O$).

Preferably, the partially neutralised heteropolyacid salts employed according to the present invention may have molecular weights of more than about 700 and less than about 8500, preferably more than about 2800 and less than about 6000. Such heteropolyacids also include dimeric complexes.

In accordance with the first aspect of the present invention, the heteropolyacid catalyst comprises a partially neutralised silicotungstic acid salt, wherein the partially neutralised silicotungstic acid salt has from 30% to 70% of the hydrogen atoms replaced with other cations. In a preferred embodiment, the proportion of hydrogen atoms replaced with other cations in the partially neutralised silicotungstic acid salt is from 40% to 60%, preferably from 45% to 55%, and more preferably from 48% to 52%, for example 50%.

In accordance with the second aspect of the present invention, the heteropolyacid catalyst comprises a partially neutralised phosphotungstic acid salt, wherein the partially neutralised phosphotungstic acid salt has from 10% to 40% of the hydrogen atoms replaced with other cations. In a preferred embodiment of the present invention the proportion of hydrogen atoms replaced with other cations in the partially neutralised phosphotungstic acid salt is from 15% to 35%.

In a one particular embodiment of both aspects, the partially neutralised heteropolyacid salt used in accordance with the present invention may comprise a partially neutralised heteropolyacid salt, wherein hydrogen atoms are replaced by an alkali metal cation other than lithium, or an alkaline earth metal cation, or mixtures thereof. However, neutralisation with lithium cations has not been found to confer the advantageous effects associated with the present invention. Preferably, the partially neutralised heteropolyacid salt has hydrogen atoms replaced by a cation selected from sodium, potassium, caesium, calcium, or mixtures thereof; more preferably caesium. In a particularly preferred embodiment of the present invention, the partially neutralised heteropolyacid salt is selected from $Cs_2H_2[SiW_{12}O_{40}].xH_2O$, $K_2H_2[SiW_{12}O_{40}].xH_2O$, $CaH_2[SiW_{12}O_{40}].xH_2O$, $Na_{0.5}H_{2.5}[PW_{12}O_{40}].xH_2O$, or $CsH_2[PW_{12}O_{40}].xH_2O$.

In other embodiments of the present invention, the partially neutralised heteropolyacid salt used in accordance with the present invention may comprise a partially neutralised heteropolyacid salt, wherein hydrogen atoms are replaced by ammonium cations, preferably $[NH_4]^+$ cations.

The supported heteropolyacid catalyst may be prepared by any means known to the skilled person. For example, it may be prepared by impregnation, precipitation or gelation. A suitable method for preparing a supported heteropolyacid catalyst is by first dissolving the chosen heteropolyacid in a suitable solvent, where suitable solvents include polar solvents such as water, ethers, alcohols, carboxylic acids, ketones and aldehydes; water and/or ethanol being the most preferable solvents. The resulting acidic solution has a heteropolyacid concentration that is preferably comprised from 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support) is the preferred method for the purposes of the present invention.

The supported partially neutralised heteropolyacid can be produced by forming various salts of the heteropolyacid in the aqueous solution either prior to, or during, impregnation of the acidic solution onto the support, by subjecting the supported heteropolyacid to a prolonged contact with a solution of a suitable metallic salt, or by addition of phosphoric acid and/or other mineral acids. The metallic salt may also preferably be impregnated onto the support, followed by subjecting the supported metallic salt to prolonged contact with a solution of the heteropolyacid.

When using a soluble metallic salt to modify the support, the salt is taken in the desired concentration, with the heteropolyacid solution. The support is then left to soak in the resulting partially neutralised acidic solution for a suitable duration (e.g. a few hours), optionally with periodic agitation or circulation, after which time it is filtered, using suitable means, in order to remove any excess acid.

When the salt is insoluble it is preferred to either impregnate the catalyst with the HPA and then titrate with the salt precursor, or to first impregnate the catalyst with the salt precursor then titrate with the HPA. The supported metallic salt or HPA may also be dried prior to titration with the solution of the HPA or metallic salt respectively. This method can improve the dispersion of the HPA salt. Other techniques such as vacuum impregnation may also be employed.

Once recovered, the impregnated support may be dried, preferably by placing the support in an oven at elevated temperature. Alternatively, or additionally, a desiccator may be employed. On a commercial scale this drying stage is often achieved by a purge of hot inert gas such as nitrogen, where a flammable solvent has been used for impregnation, or air, where an aqueous solvent has been used for impregnation.

The amount of heteropolyacid impregnated on the resulting support is suitably in the range of from 10 wt % to 80 wt % and preferably from 20 wt % to 50 wt % based on the total weight of the heteropolyacid and the support. The weight of the catalyst on drying and the weight of the support used, may be used to obtain the weight of the acid on the support by deducting the latter from the former, giving the catalyst loading as 'g heteropolyacid/kg catalyst'. The catalyst loading in 'g heteropolyacid/litre support' can also be calculated by using the known or measured bulk density of the support. The preferred catalytic loading of heteropolyacid is about 150 g to about 600 g heteropolyacid/kg Catalyst.

According to a preferred embodiment of the present invention the average heteropolyacid loading per surface area of the dried supported heteropolyacid catalyst is more than 0.1 micro moles/m$^2$.

It should be noted that the polyvalent oxidation states and hydration states of the heteropolyacids stated previously and as represented in the typical formulae of some specific compounds only apply to the fresh acid before it is impregnated onto the support, and especially before it is subjected to the dehydration process conditions. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is to be expected that such hydration and oxidation states may also be different in the spent catalysts after reaction.

According to a preferred embodiment of the present invention, the amount of chloride present in/on the said heteropolyacid supported catalyst is less than 40 ppm, preferably less than 25 ppm and most preferably less than 20 ppm.

The supported heteropolyacid catalyst used in the process of the present invention may be a fresh catalyst or a previously used catalyst. Thus, in one embodiment, at least a portion of the supported heteropolyacid catalyst has previously been employed in an alcohol dehydration process, for example in a process for the preparation of an ethene from a feed-stream comprising ethanol (and optionally water and ethoxyethane). For example, at least a portion of the supported catalyst heteropolyacid may derive from an extract of heteropolyacid from a previously used catalyst i.e. from a partially deactivated material.

Suitable catalyst supports may be in a powder form or alternatively may be in a granular form, or in a pelletised form, a spherical form or as extrudates (including shaped particles) and include, but are not limited to, clays, bentonite, diatomous earth, titania, activated carbon, aluminosilicates e.g. montmorillonite, alumina, silica-alumina, silica-titania cogels, silica-zirconia cogels, carbon coated alumina, zeolites, zinc oxide, flame pyrolysed oxides. Supports can be mixed oxides, neutral or weakly basic oxides. Silica supports are preferred, such as silica gel supports and supports produced by the flame hydrolysis of $SiCl_4$. Preferred supports are substantially free of extraneous metals or elements which might adversely affect the catalytic activity of the system. Thus, suitable silica supports are at least 99% w/w pure. Impurities amount to less than 1% w/w, preferably less than 0.60% w/w and most preferably less than 0.30% w/w. The pore volume of the support is preferably more than 0.50 ml/g and preferably more than 0.8 ml/g.

Suitable silica supports include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043. The average diameter of the support particles is about 2 to about 10 mm, preferably about 3 to about 6 mm. However, these particles may be crushed and sieved to smaller sizes of, for example, about 0.5 mm to about 2 mm, if desired. The average pore radius (prior to impregnation with the heteropolyacid) of the support is about 10 to about 500 Å, preferably about 50 to about 300 Å, more preferably about 60 to about 250 Å and most preferably about 60 to about 250 Å. The BET surface area is preferably from about 50 to about 600 $m^2/g$ and is most preferably from about 130 to about 400 $m^2/g$.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359:Part 1:1984 'Recommendations for gas adsorption (BET) methods' and BS7591:Part 2:1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380. Samples of the supports and catalysts may suitably be gassed for 16 hours at 120° C. under a vacuum of $5 \times 10^{-3}$ Torr prior to analysis.

In a further aspect, the present invention relates to a composition comprising the product obtained by any of the processes of this invention, or a derivative thereof. As this product arises from the processes of this invention, any features of the processes herein may apply, individually or in any combination, also to this aspect.

Figure 2:
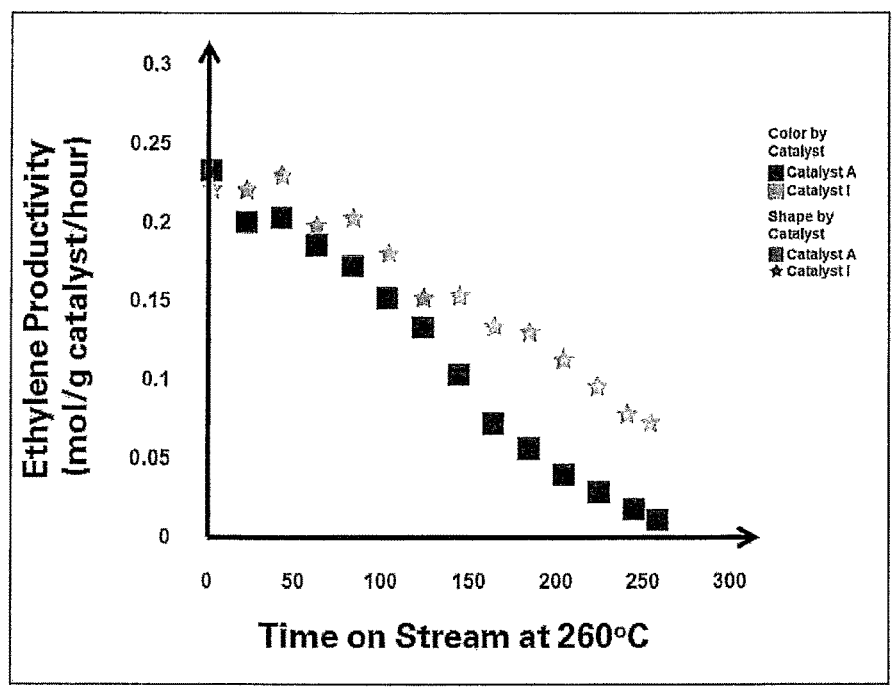
Figure 3:
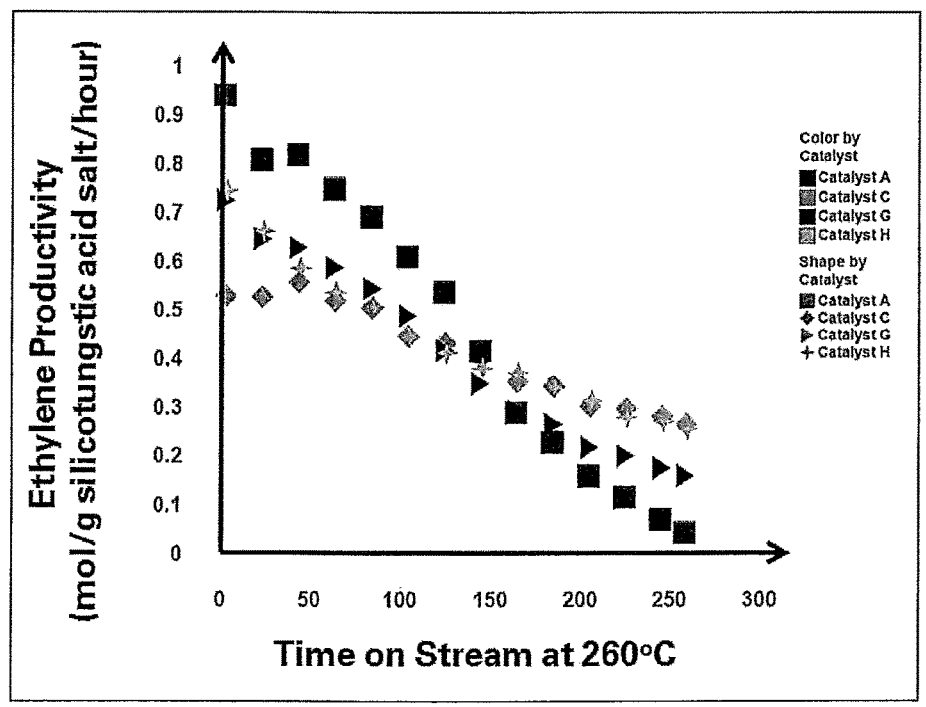
Figure 4:
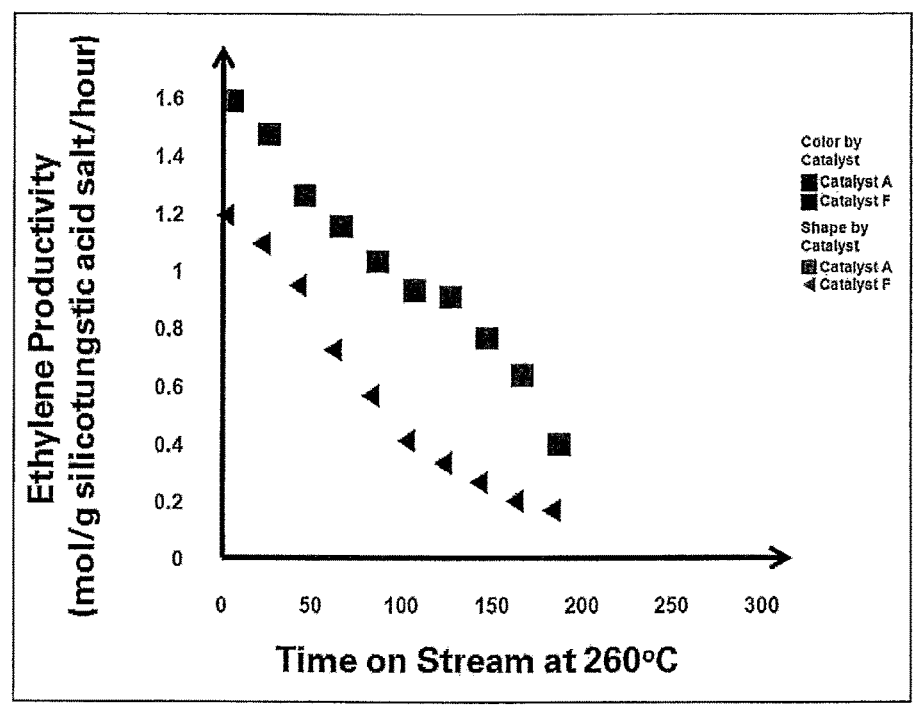
Figure 5:
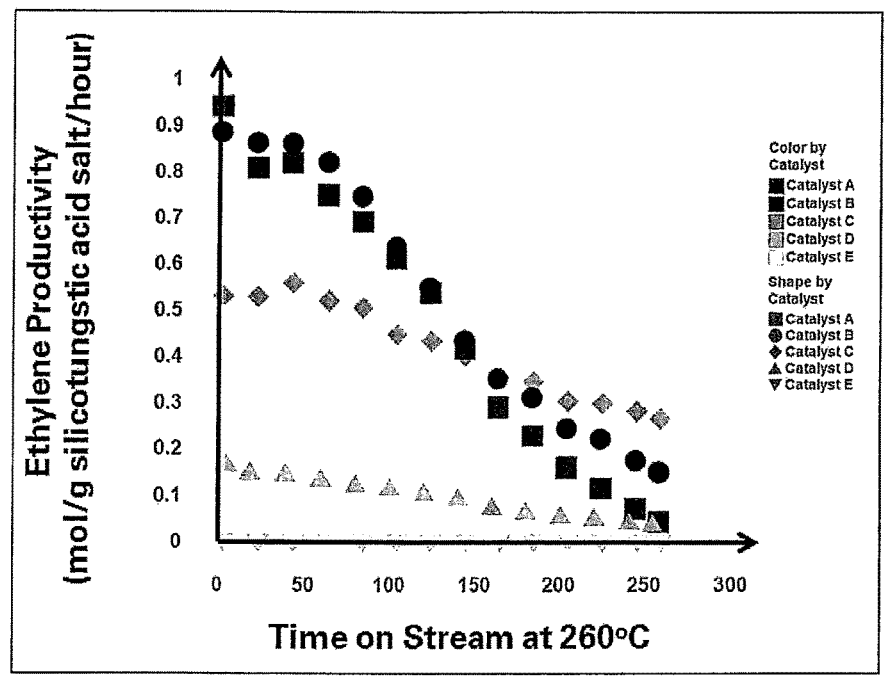
Figure 6:
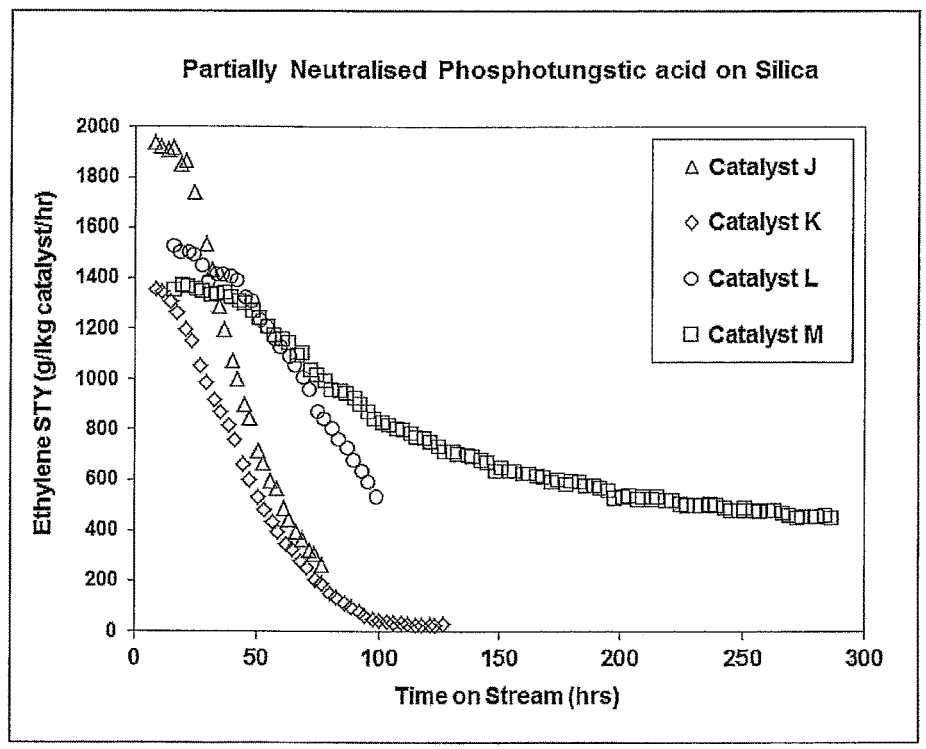

The present invention will now be illustrated by way of the following examples and with reference to the following figures:

FIG. 1: A comparison of results of the vapour phase dehydration of ethanol using catalysts A and C;

FIG. 2: A comparison of results of the vapour phase dehydration of ethanol using catalysts A and I;

FIG. 3: A comparison of results of the vapour phase dehydration of ethanol using catalysts A, C, G and H;

FIG. 4: A comparison of results of the vapour phase dehydration of ethanol using catalysts A and F;

FIG. 5: A comparison of results of the vapour phase dehydration of ethanol using catalysts A, B, C, D and E; and FIG. 6: A comparison of results of the vapour phase dehydration of ethanol using catalysts J, K, L and M.

EXAMPLES

Catalyst Preparation (Silicotungstic Acid Catalysts)

A silica support having a surface area of 156 $m^2/g$, a pore volume of 0.93 $cm^3/g$ and a mean pore diameter of 239 Å was used for the silicotungstic acid catalyst preparations.

Catalyst a (Comparative)—$H_4SiW_{12}O_{40} \cdot nH_2O$/Silica (24.5% w/w)

Silica (512 g) was added to an aqueous solution of silicotungstic acid ($H_4SiW_{12}O_{40} \cdot 24H_2O$, 508 g in 1249 g water) and allowed to remain in contact with the solution for over 60 minutes with occasional shaking. The solution was then drained from the solid, leaving the support pores filled with acid solution, and the support was dried at 110° C. for 16 hrs. The weight of the dried catalyst was 678 g.

The loading of the silicotungstic acid was calculated by the difference in weight of the silica and the final dried catalyst.

Catalyst B (Comparative)—$Cs_1H_3SiW_{12}O_{40} \cdot nH_2O$/Silica (28.5% w/w)

Silica (20.0194 g) was added to an aqueous solution of cesium carbonate (0.5958 g in 30.05 g water) and left to stand for 96 hrs before the solution was drained from the support and the solid material dried at 110° C. for 16 hrs. The weight gain of the support indicated 0.4563 g of cesium carbonate had been impregnated on to the support. The dried solid was heated under a nitrogen flow (40 ml/min) at 5° C./min from room temperature to 300° C. and held at this temperature for 5 hrs before being cooled to ambient temperature. The weight of the heat treated material was 20.3975 g.

The Cs impregnated silica was added to an aqueous solution of silicotungstic acid ($H_4SiW_{12}O_{40} \cdot 24H_2O$, 11.54 g in 28.46 g water) and allowed to contact the solution for 5 minutes. The solution was then drained from the Cs impregnated support and the remaining solution retained in the pores of the support was allowed to contact with the solid material for a further 8 hrs before the material was dried at 110° C. for 16 hrs. The weight of the dried catalyst was 28.4720 g.

The loading of the cesium-silicotungstic acid was calculated by the difference in weight of the silica and the final dried catalyst, and the Cs/silicotungstic acid ratio in the final dried catalyst was estimated to be 1.16.

Catalyst C (Example)—$Cs_2H_2SiW_{12}O_{40} \cdot nH_2O$/Silica (29.9% w/w)

Silica (20.0301 g) was added to an aqueous solution of cesium carbonate (1.1705 g in 30.14 g water) and left to stand for 96 hrs before the solution was drained from the support and the solid material dried at 110° C. for 16 hrs. The weight gain of the support indicated 0.9435 g of cesium carbonate had been impregnated on to the support. The dried solid was heated under a nitrogen flow (40 ml/min) at 5° C./min from room temperature to 300° C. and held at this temperature for 5 hrs before being cooled to ambient temperature. The weight of the heat treated material was 20.8244 g.

The Cs impregnated silica was added to aqueous solution silicotungstic acid ($H_4SiW_{12}O_{40} \cdot 24H_2O$, 11.54 g in 28.46 g water) and allowed to contact the solution for 5 minutes. The solution was then drained from the Cs impregnated support and the remaining solution retained in the pores of the support was allowed to contact with the solid material for a further 8 hrs before the material was dried at 110° C. for 16 hrs. The weight of the dried catalyst was 29.4971 g.

The loading of the cesium-silicotungstic acid was calculated by the difference in weight of the silica and the final dried catalyst, and the Cs/silicotungstic acid ratio in the final dried catalyst was estimated to be 2.25.

Catalyst D (Comparative)—$Cs_3H_1SiW_{12}O_{40} \cdot nH_2O$/Silica (29.8% w/w)

Silica (20.0277 g) was added to an aqueous solution of cesium carbonate (1.7484 g in 29.97 g water) and left to stand for 96 hrs before the solution was drained from the support and the solid material dried at 110° C. for 16 hrs. The weight gain of the support indicated 1.3291 g of cesium carbonate had been impregnated on to the support. The dried solid was heated under a nitrogen flow (40 ml/min) at 5° C./min from room temperature to 300° C. and held at this temperature for 5 hrs before being cooled to ambient temperature. The weight of the heat treated material was 21.2103 g.

The Cs impregnated silica was added to aqueous solution silicotungstic acid ($H_4SiW_{12}O_{40} \cdot 24H_2O$, 11.54 g in 28.46 g water) and allowed to contact the solution for 5 minutes. The solution was then drained from the Cs impregnated support and the remaining solution retained in the pores of the support was allowed to contact with the solid material for a further 8 hrs before the material was dried at 110° C. for 16 hrs. The weight of the dried catalyst was 29.8569 g.

The loading of the cesium-silicotungstic acid was calculated by the difference in weight of the silica and the final dried catalyst, and the Cs/silicotungstic acid ratio in the final dried catalyst was estimated to be 3.18.

Catalyst E (Comparative)—$Cs_4H_0SiW_{12}O_{40} \cdot nH_2O$/Silica (26.2% w/w)

Silica (20.0471 g) was added to an aqueous solution of cesium carbonate (2.3554 g in 30.05 g water) and left to stand for 96 hrs before the solution was drained from the support and the solid material dried at 110° C. for 16 hrs. The weight gain of the support indicated 1.8366 g of cesium carbonate had been impregnated on to the support. The dried solid was heated under a nitrogen flow (40 ml/min) at 5° C./min from room temperature to 300° C. and held at this temperature for 5 hrs before being cooled to ambient temperature. The weight of the heat treated material was 21.6451 g.

The Cs impregnated silica was added to an aqueous solution of silicotungstic acid ($H_4SiW_{12}O_{40} \cdot 24H_2O$, 11.54 g in 28.46 g water) and allowed to contact the solution for 5 minutes. The solution was then drained from the Cs impregnated support and the remaining solution retained in the pores of the support was allowed to contact with the solid material for a further 8 hrs before the material was dried at 110° C. for 16 hrs. The weight of the dried catalyst was 29.0184 g.

The loading of the cesium-silicotungstic acid was calculated by the difference in weight of the silica and the final dried catalyst, and the Cs/silicotungstic acid ratio in the final dried catalyst was estimated to be 5.23.

Catalyst F (Comparative)—$Li_2H_2SiW_{12}O_{40} \cdot nH_2O$/Silica (25.2% w/w)

An aqueous solution of lithium carbonate (0.4487 g in 29.97 g of water) was added to an aqueous solution of silicotungstic acid (19.83 g in 18.89 g of water) with vigorous stirring. After 2 hrs silica (20.0951 g) was added to the lithium-silicotungstic acid solution and left in contact for 24 hrs before the solution was drained. The solid was then dried at 110° C. for 16 hrs. The weight of dried catalyst was 26.8892 g.

The loading of the lithium-silicotungstic acid was calculated by the difference in weight of the silica and the final dried catalyst, and the Li/silicotungstic acid ratio in the final dried catalyst was calculated to be 2.03.

Catalyst G (Example)—$K_2H_2SiW_{12}O_{40} \cdot nH_2O$/Silica (24.1% w/w)

An aqueous solution of potassium carbonate (0.8292 g in 29.93 g of water) was added to an aqueous solution of silicotungstic acid (19.81 g in 0.8292 g of water) with vigorous stirring. After 2 hrs silica (19.9776 g) was added to the potassium-silicotungstic acid solution and left in contact for 24 hrs before the solution was drained. The solid was then dried at 110° C. for 16 hrs.

The loading of the potassium-silicotungstic acid was calculated by the difference in weight of the silica and the final dried catalyst, and the K/silicotungstic acid ratio in the final dried catalyst was calculated to be 2.01.

Catalyst H (Example)—$Ca_1H_2SiW_{12}O_{40} \cdot nH_2O$/Silica (24.0% w/w)

An aqueous solution of calcium nitrate (1.4270 g in 30.02 g of water) was added to an aqueous solution of silicotungstic acid (19.8 g in 18.82 g of water) vigorous stirring. After 2 hrs silica (19.9959 g) was added to the calcium-silicotungstic acid solution and left in contact for 24 hrs before the solution was drained. The solid was then dried at 110° C. for 16 hrs.

The loading of the calcium-silicotungstic acid was calculated by the difference in weight of the silica and the final dried catalyst, and the Ca/silicotungstic acid ratio in the final dried catalyst was estimated to be 1.01.

Catalyst I (Example)—$Cs_2H_2SiW_{12}O_{40} \cdot nH_2O$/Silica (45.5% w/w)

Silica (20.03 g) was added to an aqueous solution of cesium carbonate (2.3442 g in 30.05 g water) and left to stand for 96 hrs before the solution was drained from the support and the solid material dried at 110° C. for 16 hrs. The weight gain of the support indicated 1.88 g of cesium carbonate had been impregnated on to the support. A portion of the dried solid (13.55 g) was heated under a nitrogen flow (40 ml/min) at 5° C./min from room temperature to 300° C. and held at this temperature for 5 hrs before being cooled to ambient temperature. The weight of the heat treated material was 13.40 g.

A portion of the Cs impregnated silica (10.94 g) was added to an aqueous solution of silicotungstic acid ($H_4SiW_{12}O_{40} \cdot 24H_2O$, 21.50 g in 26.68 g water) and allowed to contact the solution for 5 minutes. The solution was then drained from the Cs impregnated support and the remaining solution retained in the pores of the support was allowed to contact with the solid material for a further 5 minutes before the material was dried at 110° C. for 16 hrs. The weight of the dried catalyst was 19.30 g.

The loading of the cesium-silicotungstic acid was calculated by the difference in weight of the silica and the final dried catalyst, and the Cs/silicotungstic acid ratio in the final dried catalyst was estimated to be 2.28.

A silica support having a surface area of 182 m2/g, a pore volume of 1.00 cm3/g and a mean pore diameter of 219 Å was used for the phosphotungstic tungstic acid catalyst preparations.

Catalyst Preparation (Phosphotungstic Acid Catalysts)

Catalyst J (Comparative)—$H_3PW_{12}O_{40} \cdot nH_2O$/Silica (27.2% w/w)

Silica (43.0 g) was added to an aqueous solution of phosphotungstic acid ($H_3PW_{12}O_{40} \cdot 24H_2O$, 43.0 g in 97.6 g water) and allowed to remain in contact with the solution for 1 hr. The solution was then drained from the solid, leaving the support pores filled with acid solution, and the support was dried at 130° C. for 16 hrs. The weight of the dried catalyst was 16.1 g.

The loading of the phosphotungstic acid was calculated by the difference in weight of the silica and the final dried catalyst.

Catalyst K (Comparative)—$Li_{0.5}H_{2.5}PW_{12}O_{40} \cdot nH_2O$/Silica (25.9% w/w)

An aqueous solution of lithium carbonate (0.0417 g in 5.0242 g of water) was added to an aqueous solution of phosphotungstic acid ($H_3PW_{12}O_{40} \cdot 24H_2O$, 6.2538 g in 6.2538 g of water) with stirring. After 10 minutes, silica (6.4532 g) was added to the lithium-phosphotungstic acid solution and left in contact for 1 hr before the solution was drained. The solid was then dried at 130° C. for 16 hrs. The weight of dried catalyst was 8.7141 g.

The loading of the lithium-phosphotungstic acid was calculated the by difference in weight of the silica and the final dried catalyst, and the Li/phosphotungstic acid ratio in the final dried catalyst was calculated to be 0.60.

Catalyst L (Example)—$Na_{0.5}H_{2.5}PW_{12}O_{40} \cdot nH_2O$/Silica (26.0% w/w)

An aqueous solution of sodium carbonate (0.0560 g in 4.9135 g of water) was added to an aqueous solution of phosphotungstic acid ($H_3PW_{12}O_{40} \cdot 24H_2O$, 6.2727 g in 9.8199 g of water) with stirring. After 10 minutes, silica (6.4451 g) was added to the sodium-phosphotungstic acid solution and left in contact for 1 hr before the solution was drained. The solid was then dried at 130° C. for 16 hrs. The weight of dried catalyst was 8.7062.

The loading of the sodium-phosphotungstic acid was calculated by the difference in weight of the silica and the final dried catalyst, and the Na/phosphotungstic acid ratio in the final dried catalyst was calculated to be 0.56.

Catalyst M (Example)—$Cs_1H_2PW_{12}O_{40} \cdot nH_2O$/Silica (27.4% w/w)

Silica (6.5286 g) was added to an aqueous solution of cesium carbonate (0.3130 g in 7.2836 g water) and left to stand for 1 hr before the solution was drained from the support and the solid material dried at 130° C. for 16 hrs.

The Cs impregnated silica was added to an aqueous solution of phosphotungstic acid ($H_3PW_{12}O_{40} \cdot 24H_2O$, 2.8272 g in 12.8920 g water) and allowed to contact the solution for 1 hr. The solution was then drained from the Cs impregnated support and was dried at 130° C. for 16 hrs.

The loading of the cesium-phosphotungstic acid was calculated by the difference in weight of the silica and the final dried catalyst and the Cs/phosphotungstic acid ratio in the final dried catalyst was estimated to be 1.56.

TABLE 1

Summary of Catalyst Compositions for Catalysts A to M

| Catalyst | Catalyst Composition | Mass of catalyst (mg) | Tests Data used in |
|---|---|---|---|
| A | $H_4SiW_{12}O_{40} \cdot xH_2O$/Silica (24.5 wt %) | 108.54 | Example 1, 2, 3, 5 |
| A | $H_4SiW_{12}O_{40} \cdot xH_2O$/Silica (24.5 wt %) | 27.3 | Example 4 |
| B | $Cs_1H_3SiW_{12}O_{40} \cdot xH_2O$/Silica (28.5 wt %) | 64.2 | Example 5 |
| C | $Cs_2H_2SiW_{12}O_{40} \cdot xH_2O$/Silica (29.9 wt %) | 92.14 | Example 1, 3 |
| D | $Cs_3H_1SiW_{12}O_{40} \cdot xH_2O$/Silica (29.8 wt %) | 91.2 | Example 5 |
| E | $Cs_4H_0SiW_{12}O_{40} \cdot xH_2O$/Silica (26.2 wt %) | 90.24 | Example 5 |
| F | $Li_2H_2SiW_{12}O_{40} \cdot xH_2O$/Silica (25.2 wt %) | 53.4 | Example 4 |
| G | $K_2H_2SiW_{12}O_{40} \cdot xH_2O$/Silica (24.1 wt %) | 113.97 | Example 3 |
| H | $Ca_1H_2SiW_{12}O_{40} \cdot xH_2O$/Silica (24.0 wt %) | 114.72 | Example 3 |
| I | $Cs_2H_2SiW_{12}O_{40} \cdot xH_2O$/Silica (45.5 wt %) | 60.4 | Example 2 |
| J | $H_3PW_{12}O_{40} \cdot nH_2O$/Silica (27.2 wt %) | 2701 | Example 6 |
| K | $Li_{0.5}H_{2.5}PW_{12}O_{40} \cdot nH_2O$/Silica 25.9 wt %) | 4424 | Example 6 |
| L | $Na_{0.5}H_{2.5}PW_{12}O_{40} \cdot nH_2O$/Silica (26.0 t %) | 4420 | Example 6 |
| M | $Cs_{1.0}H_{2.0}PW_{12}O_{40} \cdot nH_2O$/Silica (27.4 wt %) | 4614 | Example 6 |

General Procedure for Vapour Phase Dehydration of Ethanol with Silicotungstic Acid Catalysts A to I:

A mass of silicotungstic acid catalyst shown in Table 1 above (A to I), having 100-200 μm particle diameter and prepared in accordance with the above methods, was loaded into a reactor tube having an isothermal bed and pressurised to 0.501 MPa under an inert gas (nitrogen and helium) flow. The catalyst was heated at 2° C./min to 240° C. under a combined nitrogen (0.01500 mol/hr) and helium flow (0.00107 mol/hr) and held at this temperature for 8 hours before being cooled to 150° C.

Ethanol (0.04084 mol/hr) was then added to the nitrogen/helium flow and the temperature was increased at 2° C./min to 225° C. Once at 225° C. the feed pressure was increased at a rate of 0.1 MPa/min such that the pressure inside the reactor was increased to the value of 2.858 MPa. The diethyl ether and water reagents were then added to the ethanol, helium and nitrogen flow. At this point the flows of the feed components were adjusted to give ethanol (0.02677 mol/hr), diethyl ether (0.00776 mol/hr), water (0.00297 mol/hr), helium (0.00106 mol/hr) and nitrogen (0.01479 mol/hr).

Once the catalyst performance had stabilised to a steady-state at 225° C., typically after around 100 hrs, the catalyst temperature, which is the same as the feed temperature in this particular reactor, was increased to 260° C. and the ethylene productivity monitored versus time by on-line GC analysis for up to 260 hours.

Example 1

Vapour phase dehydration of ethanol was conducted independently with catalysts A and C according to the above procedure. The results of the reactions are illustrated graphically in FIG. 1. These results show the benefit of 50% neutralization by cesium per unit mass of silicotungstic acid salt compared to the free acid for similar loading of silicotungstic acid on the support. These results illustrate that, in contrast to the free acid, a partially neutralized silicotungstic acid catalyst according to the invention retains at least 25% of its maximum activity, observed for the same operating conditions, even after 200 hours of operation of the process with the same catalyst under the same conditions and without regeneration.

Example 2

Vapour phase dehydration of ethanol was conducted independently with catalysts A and I according to the above procedure. The results of the reactions are illustrated graphically in FIG. 2. These results show the benefit to catalyst lifetime of 50% neutralization by cesium at increased loading, which affords the same initial activity per unit mass catalyst as the free acid analogue. These results illustrate that, in contrast to the free acid, a partially neutralized silicotungstic acid catalyst according to the invention retains at least 25% of its maximum activity, observed for the same operating conditions, even after 200 hours of operation of the process with the same catalyst under the same conditions and without regeneration.

Example 3

Vapour phase dehydration of ethanol was conducted independently with catalysts A, C, G and H according to the above procedure. The results of the reactions are illustrated graphically in FIG. 3. These results show the benefit to catalyst lifetime of 50% neutralization by cesium, potassium and calcium per unit mass of silicotungstic acid salt compared to the free acid, for similar loading of silicotungstic acid. These results illustrate that, in contrast to the free acid, a partially neutralized silicotungstic acid catalyst according to the invention retains at least 25% of its maximum activity, observed for the same operating conditions, even after 200 hours of operation of the process with the same catalyst under the same conditions and without regeneration.

Example 4

Vapour phase dehydration of ethanol was conducted independently with catalysts A and F according to the above procedure. The results of the reactions are illustrated graphically in FIG. 4. These results show that no benefit is observed with 50% neutralization by lithium compared to the free acid for similar loading.

Example 5

Vapour phase dehydration of ethanol was conducted independently with catalysts A, B, C, D and E according to the above procedure. The results of the reactions are illustrated graphically in FIG. 5. These results show the optimum benefit to catalyst lifetime is with 50% neutralization for a series of cesium containing catalysts. These results illustrate that, in contrast to the free acid, a partially neutralized silicotungstic acid catalyst according to the invention retains at least 25% of its maximum activity, observed for the same operating conditions, even after 200 hours of operation of the process with the same catalyst under the same conditions and without regeneration.

General Procedure for Vapour Phase Dehydration of Ethanol with Phosphotungstic Acid Catalysts J to M:

A mass of phosphotungstic acid catalyst, shown in Table 1 above (J to M), prepared in accordance with the above method was loaded into a reactor tube and pressurized to 0.5 MPa under nitrogen gas flow.

The catalyst was heated at to 240° C. under a nitrogen flow (0.0375 mol/ml catalyst/hr) and held at this temperature for between 22 and 24 hrs. The catalyst was subsequently steamed under a water (0.0178 mol/ml catalyst/hr) and nitrogen flow (0.0375 mol/ml catalyst/hr) for between 17 and 19 hrs before this was replaced by a feed comprising ethanol (0.0141 mol/ml catalyst/hr), water (0.0180 mol/ml catalyst/hr) and nitrogen (0.0352 mol/ml catalyst hr). After approximately 3 hrs the this feed was replaced by one comprising ethanol (0.0310 mol/ml catalyst/hr), water (0.0087 mol/ml catalyst/hr) and nitrogen (0.0307 mol/ml catalyst hr) and the pressure increased to 0.7 MPa. After 90 minutes under these conditions the pressure was increased to 3.1 MPa and the feed was replaced by one containing ethanol (0.0512 mol/ml catalyst/hr), diethyl ether (0.0322 mol/ml catalyst/hr), water (0.0117 mol/ml catalyst/hr) and nitrogen (0.0429 mol/ml catalyst/hr). After a further 15 minutes the temperature was increased to 250° C. The catalyst was operated at steady state under these conditions for up to 290 hrs. The ethylene productivity was monitored versus time by on-line GC analysis.

Example 6

Vapour phase dehydration of ethanol was conducted independently with catalysts J, K, L and M according to the above procedure. The results of the reactions are illustrated graphically in FIG. 6. These results show the benefit to catalyst lifetime of neutralization by alkali metals other than lithium of phosphotungstic acid, compared to the free acid per unit mass of PTA salt for similar levels of loading. These results also illustrate that, in contrast to the free acid, a partially neutralized phosphotungstic acid catalyst (M) according to the invention retains at least 25% of its maximum activity, observed for the same operating conditions, after 150 hours of operation of the process with the same catalyst under the same conditions and without regeneration.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for vapour phase chemical dehydration of ethanol in a reactor in the presence of a supported heteropolyacid catalyst, said process comprising:
   a) contacting the ethanol with the supported heteropolyacid catalyst,
   wherein the supported heteropolyacid catalyst comprises:
      a partially neutralised silicotungstic acid salt, wherein the partially neutralised silicotungstic acid salt has from 30% to 70% of the hydrogen atoms replaced with cations selected from the group consisting of alkali metal cations, alkaline earth metal cations, transition metal cations, ammonium cations, and mixtures thereof; but with the proviso that the alkali metal cation is not lithium;
b) attaining steady-state performance of the catalyst;
c) operating continuously with the supported heteropolyacid catalyst for at least 150 hours, without any regeneration of the supported heteropolyacid catalyst.

2. A process according to claim 1, wherein the proportion of hydrogen atoms replaced with other cations in the partially neutralised silicotungstic acid salt is from 40% to 60%.

3. A process according to claim 1, wherein the catalyst retains at least 25% of its maximum activity observed for the operating temperature under steady-state conditions after at least 200 hours of operation of the process.

4. A process according to claim 1, wherein the partially neutralised silicotungstic acid salt has hydrogen atoms replaced by alkali metal cations, alkaline earth metal cations, or mixtures thereof.

5. A process according to claim 1, wherein the partially neutralised silicotungstic acid salt has hydrogen atoms replaced by cations selected from sodium, potassium, caesium, calcium or mixtures thereof.

6. A process according to claim 1, wherein the partially neutralised silicotungstic acid salt has hydrogen atoms replaced by ammonium cations.

7. A process according to claim 1, wherein the acid loading on the support is in the range of 10 wt % to 80 wt %, based on the total weight of the supported catalyst.

8. A process according to claim 1, wherein the catalyst support of the supported heteropolyacid catalyst is a silica support.

9. A process according to claim 1, wherein operating continuously in step c) is for at least 200 hours without any regeneration of the supported heteropolyacid catalyst.

10. A process according to claim 1, wherein the feed temperature of the feed-stream comprising ethanol is from 180° C. to 270° C.

11. A process according to claim 1, wherein the process is operated at an internal reactor pressure of from 0.1 MPa to 4.5 MPa.

12. A process according to claim 1, wherein the catalyst retains at least 85% of its maximum activity observed for the operating temperature under steady-state conditions after at least 200 hours of operation of the process.

13. A process according to claim 1, wherein the partially neutralised silicotungstic acid salt has hydrogen atoms replaced by caesium cations.

14. A process according to claim 1, wherein operating continuously in step c) is for at least 250 hours, without any regeneration of the supported heteropolyacid catalyst.

15. A method for increasing catalyst lifetime of a supported partially neutralised heteropolyacid catalyst in an alcohol dehydration process, said method comprising supplying to an alcohol dehydration process a supported partially neutralised heteropolyacid catalyst, wherein the partially neutralised heteropolyacid catalyst comprises a partially neutralised silicotungstic acid salt having from 30% to 70% of the hydrogen atoms replaced with cations selected from the group consisting of alkali metal cations, alkaline earth metal cations, transition metal cations, ammonium cations, and mixtures thereof, but with the proviso that the alkali metal cation is not lithium.

16. A method according to claim 15, wherein the alcohol dehydration process is an ethanol dehydration process.

* * * * *